United States Patent
Hayashi et al.

(10) Patent No.: US 8,049,185 B2
(45) Date of Patent: Nov. 1, 2011

(54) FLUORESCENCE DETECTION DEVICE AND FLUORESCENCE DETECTION METHOD

(75) Inventors: Hironori Hayashi, Tamano (JP); Shigeyuki Nakada, Tamano (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 0 days.

(21) Appl. No.: 12/866,265

(22) PCT Filed: Feb. 4, 2009

(86) PCT No.: PCT/JP2009/000424
§ 371 (c)(1),
(2), (4) Date: Aug. 5, 2010

(87) PCT Pub. No.: WO2009/098868
PCT Pub. Date: Aug. 13, 2009

(65) Prior Publication Data
US 2010/0314557 A1    Dec. 16, 2010

(30) Foreign Application Priority Data
Feb. 7, 2008    (JP) .................................. 2008-027352

(51) Int. Cl.
*G01N 21/64*    (2006.01)
(52) U.S. Cl. .................................................. 250/459.1
(58) Field of Classification Search ................. 250/459.1
See application file for complete search history.

(56) References Cited

U.S. PATENT DOCUMENTS

| 4,643,566 A | 2/1987 | Ohe et al. |
| 5,315,122 A * | 5/1994 | Pinsky et al. ............... 250/461.2 |
| 5,480,775 A | 1/1996 | Ito et al. |

FOREIGN PATENT DOCUMENTS

| JP | 61-029738 A | 2/1986 |
| JP | 61-128140 A | 6/1986 |
| JP | 03-221837 A | 9/1991 |
| JP | 09-096603 A | 4/1997 |
| JP | 2006226698 A * | 8/2006 |

OTHER PUBLICATIONS

Beckman Coulter, Inc., "Introduction to Principles of FCM-VI", Japanese website, http://www.bc-cytometry.com/FCM/fcmprinciple_6-6.html, searched on Dec. 6, 2007.

Yamazaki et al., "Laser ni yoru Bisho Ryushi Bunseki Gijyutsu no Kairyo", Transactions of the Japan Society of Mechanical Engineers, Series C, May 1994, vol. 60, No. 573, pp. 122-127.

* cited by examiner

*Primary Examiner* — Kiho Kim
(74) *Attorney, Agent, or Firm* — Global IP Counselors, LLP (57) ABSTRACT

In a fluorescence detection device and a fluorescence detection method, forward-scattered light which is scattered from a measurement object irradiated with a laser beam is received and detection signals for informing the measurement object passing through the measurement point and for identifying a focus position of the forward-scattered light are produced. While, fluorescence emitted by the measurement object is received through a collecting lens and a light-reception signal of the fluorescence is outputted. The fluorescence intensity level is outputted based on the outputted light-reception signal and the produced detection signals. A focus position of the forward-scattered light is identified from the produced detection signals and the light reception-signal is corrected using a correction coefficient corresponding to the identified focus position.

9 Claims, 5 Drawing Sheets

FLUORESCENCE DETECTION DEVICE AND FLUORESCENCE DETECTION METHOD

CROSS-REFERENCE TO RELATED APPLICATIONS

This U.S. National stage application claims priority under 35 U.S.C. §119(a) to Japanese Patent Application No. 2008-027352, filed in Japan on Feb. 7, 2008, the entire contents of which are hereby incorporated herein by reference.

TECHNICAL FIELD

The present invention relates to a fluorescence detection device and a fluorescence detection method of measuring fluorescence emitted from a measurement object flowing through a flow channel by irradiation with a laser beam.

BACKGROUND ART

A flow cytometer used in medical and biological fields includes a fluorescence detection device that receives fluorescence emitted from a fluorochrome attached to a measurement object by irradiation with a laser beam to identify the type of the measurement object.

A laser beam used in such a fluorescence detection device generally has a Gaussian intensity distribution, and therefore its light intensity is high at the center but decreases toward the edge. In order to accurately measure fluorescence with high resolution by a fluorescence detection device, it is necessary to irradiate a measurement object with a laser beam at a uniform intensity. Therefore, when a laser beam having a Gaussian intensity distribution is used, the central part of the laser beam where the light intensity is substantially uniform is used to irradiate a measurement object. However, when passing through a predetermined measurement point in a flow channel, a measurement object flowing through the flow channel is displaced from the center of the measurement point. Therefore, attempts have been made to minimize the amount of displacement of a measurement object from the center of a measurement point. Further, attempts to expand a portion of a laser beam having a Gaussian intensity distribution where the light intensity is uniform have been made by increasing the width of the laser beam.

The online article "Introduction to Principles of FCM-VI," which could be found at http://www.bc-cytometry.com/FCM/fcmprinciple_6-6.html on Dec. 6, 2007, discloses a flow cytometer and describes that the flow cytometer needs to satisfy the following requirements to achieve high measurement resolution: stabilization of the light intensity of a laser beam; reduction in the diameter of a stream of a sheath liquid allowed to flow together with a measurement object; and formation of a laminar flow of the sheath liquid.

However, high measurement resolution and efficient use of a laser beam cannot be achieved only by satisfying the above requirements, that is, stabilization of the light intensity of a laser beam, reduction in the diameter of a stream of a sheath liquid, and formation of a laminar flow of the sheath liquid.

For example, a part of a laser beam having a uniform light intensity and used for measuring a measurement object can be expanded by increasing the width of the laser beam, but an outer portion of the laser beam is not used to irradiate the measurement object, which is disadvantageous from the viewpoint of efficient use of a laser beam.

DISCLOSURE OF THE INVENTION

Problems to be Solved by the Invention

In order to solve the above problem, an object of the present invention is to provide a fluorescence detection device and a fluorescence detection method of measuring fluorescence emitted from a measurement object flowing through a flow channel by irradiation with a laser beam, which are capable of improving laser beam-use efficiency and of obtaining high-resolution results from measured data.

The present invention provides a fluorescence detection device for measuring fluorescence emitted from a measurement object flowing through a flow channel by irradiation with a laser light, including:

a laser light source unit that irradiates, with a laser beam, a measurement object passing through a measurement point in a flow channel;

a first light-receiving unit comprising an optical system that collects forward-scattered laser light from the measurement object and a plurality of detectors arranged side by side in a direction perpendicular to a direction of an optical axis of the laser beam and to a direction in which the measurement object flows through the flow channel in order to receive the collected forward-scattered light to inform the timing of passage of the measurement object through the measurement point and to detect a focus position of the collected forward-scattered light;

a second light-receiving unit that receives, through a collecting lens, fluorescence emitted from the measurement object irradiated with the laser beam and outputs a light-reception signal; and a processing unit that uses one of detection signals outputted from the first light-receiving unit as a trigger signal to start data processing performed based on the light-reception signal outputted from the second light-receiving unit and the detection signal, and outputs an output value of fluorescence intensity, wherein the processing unit identifies a focus position of the forward-scattered light based on the detection signals outputted from the first light-receiving unit and determines, based on the thus determined focus position, a correction factor for correcting the light-reception signal outputted from the second light-receiving unit, and corrects the light-reception signal using the correction factor.

The processing unit preferably determines the correction factor using a correction table obtained by making a linkage between the focus position and the correction factor for correcting a light-reception signal based on information of light intensity distribution of the laser beam with which the measurement object is irradiated.

Preferably, the fluorescence detection device further includes a shielding plate provided between the flow channel and the first light-receiving unit to block a portion of the laser beam around an optical axis of the laser beam to prevent the first light-receiving unit from being irradiated with direct light of the laser beam.

Also preferably, the fluorescence detection device further includes an analyzer that creates a frequency distribution of fluorescence intensity using the corrected light-reception signal when a plurality of measurement objects are allowed to flow through the flow channel one after another.

Also preferably, the fluorescence detection device further includes an analyzer that determines a size of the measurement object using an intensity of a scattered-light signal of the forward-scattered light outputted from the first light-receiving unit and the focus position of the forward-scattered light.

The present invention provides a fluorescence detection method of measuring fluorescence emitted from a measurement object flowing through a flow channel by irradiation with a laser light, including the steps of:

irradiating, with a laser light, a measurement object allowed to flow through a flow channel so as to pass through a measurement point in the flow channel;

producing detection signals for detecting a focus position of forward-scattered laser light collected by an optical system when the measurement object passes through the measurement point;

receiving, through a collecting lens, fluorescence emitted from the measurement object irradiated with the laser beam and outputting a light-reception signal; and identifying a focus position of the forward-scattered light based on the detection signals, and determining, based on the thus identified focus position, a correction factor for correcting the light-reception signal, and correcting the light-reception signal using the correction factor to calculate fluorescence intensity.

In the present invention, when the light-reception signal is corrected, the correction factor is preferably determined using a correction table obtained by making a linkage between the focus position and the correction factor for correcting a light-reception signal based on information about light intensity distribution of the laser beam with which the measurement object is irradiated.

Also preferably, the fluorescence detection method further includes the step of creating a frequency distribution of fluorescence intensity using the corrected light reception signal when a plurality of measurement objects are allowed to flow through the flow channel one after another.

Also preferably, the fluorescence detection method further includes the step of determining a size of the measurement object using an intensity of a scattered-light signal of the forward-scattered light and the focus position of the forward-scattered light.

Effects of the Invention

In the fluorescence detection device and the fluorescence detection method according to the present invention, the first light-receiving unit that collects forward-scattered laser light from a measurement object to inform the timing of passage of the measurement object through a measurement point in a flow channel is equipped with a plurality of detectors for detecting the focus position of the collected forward-scattered light. The detectors are arranged side by side in a direction perpendicular to the direction of the optical axis of a laser beam and to a direction in which the measurement object flows through the flow channel. Thereby the processing unit can identify the focus position of forward-scattered light based on a detection signal outputted from the first light-receiving unit, and to determine, based on the thus identified focus position, a correction factor for correcting a light-reception signal outputted from the second light-receiving unit, and to correct the light-reception signal using the correction factor. Therefore, even when a laser beam having a Gaussian intensity distribution is used, not only the central portion of the laser beam where the light intensity is uniform but also the outer portion of the laser beam where the light intensity is significantly decreased can be used to irradiate a measurement object, thereby improving laser beam-use efficiency.

Further, the correction of a light-reception signal makes it possible for the analyzer to create a sharp frequency distribution of fluorescence intensity (i.e., a frequency distribution with a low variance of the values of fluorescence intensity).

Therefore, even in a case where two peaks close to each other appear in a frequency distribution, the resolution of an obtained result is high to such an extent that the two peaks can be discriminated from each other.

BEST MODE FOR CARRYING OUT THE INVENTION

Hereinbelow, a fluorescence detection device and a fluorescence detection method according to the present invention will be described in detail.

Figure 1:
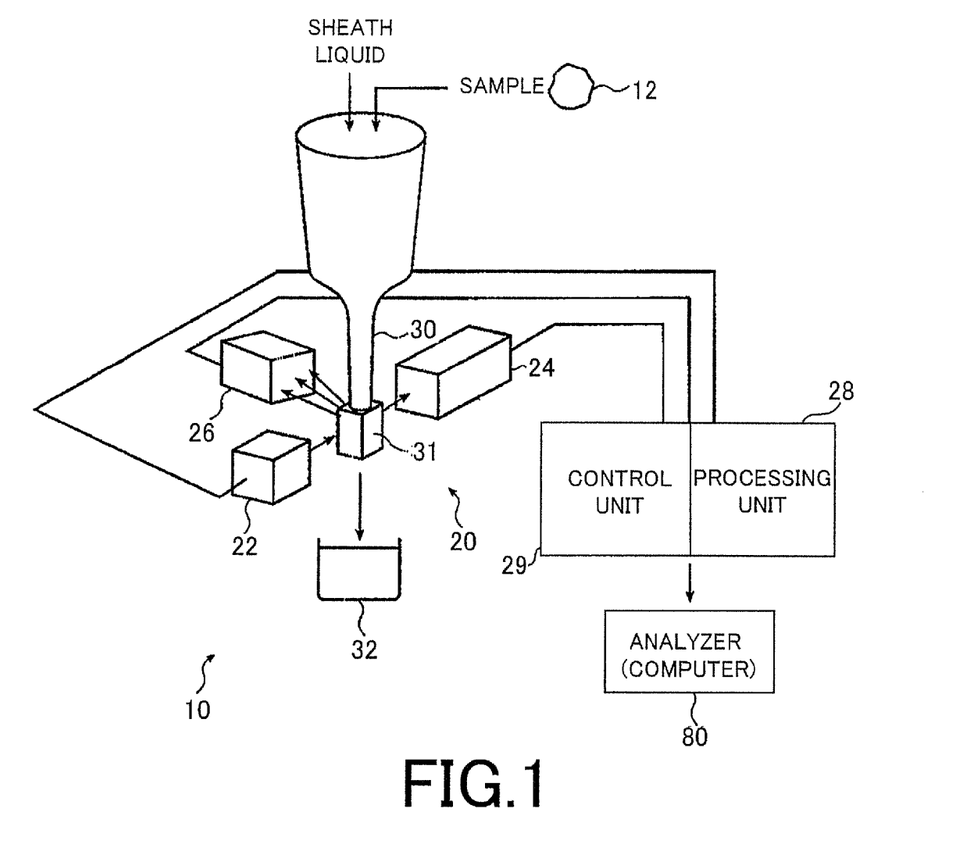
FIG. 1 is a schematic view illustrating the composition of a flow cytometer using a fluorescence detection device according to the present invention.

FIG. 1 is a schematic view illustrating the composition of a flow cytometer 10 using the fluorescence detection device according to the present invention.

The flow cytometer 10 includes a signal processor (fluorescence detection device) 20 and an analyzer 80. The signal processor 20 irradiates a sample 12 to be measured such as a cell with a laser beam to detect fluorescence emitted from a part of the sample 12 and performs signal processing. The analyzer 80 analyzes a measurement object contained in the sample 12 based on processing results obtained by the signal processor 20.

The signal processor 20 includes a laser light source unit 22, light-receiving units 24 and 26, a processing unit 28, a control unit 29, a tube 30, and a flow cell body 31.

The processing unit 28 outputs an output value of intensity of fluorescence emitted from the sample 12. The control unit 29 allows the laser light source unit 22 to emit a laser beam at a predetermined intensity, and controls various processing operations performed by the processing unit 28. The tube 30 allows the sample 12 to flow through it together with a sheath liquid that forms a high-speed stream. The flow cell body 31 is connected to the end of the tube 30 to form a flow of the sample 12. In a flow channel through which the sample 12 flows, a measurement point irradiated with a laser beam is provided.

On the output side of the flow cell body 31, a recovery container 32 is provided. The flow cytometer 10 may be provided with a cell sorter for separating specific cells or the like contained in the sample 12 in a short period of time after irradiation with a laser beam. In this case, two or more recovery containers are provided to collect separated cells.

The laser light source unit 22 emits three beams of laser light having different wavelengths (e.g., $\lambda_1=405$ nm, $\lambda_2=533$ nm, $\lambda_3=650$ nm). The laser beams are focused by a lens system on a predetermined position in the flow cell body 31. This focus position corresponds to the measurement point of the sample 12.

Figure 2:
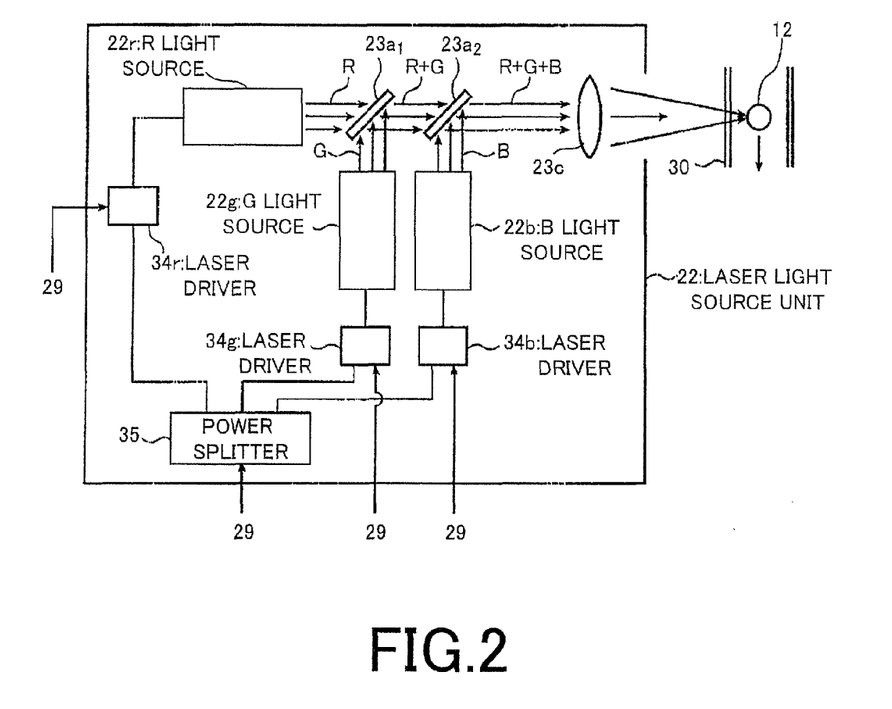
FIG. 2 is a schematic view illustrating the composition of one example of a laser light source unit used in the fluorescence detection device according to the present invention.

FIG. 2 is a schematic view illustrating one example of the composition of the laser light source unit 22.

The laser light source unit 22 includes an R light source 22r, a G light source 22g, a B light source 22b, dichroic mirrors $23a_1$ and $23a_2$, a lens system 23c, laser drivers 34r, 34g, and 34b, and a power splitter 35.

Each of the R light source 22r, the G light source 22g, and the B light source 22b emits a laser beam having a visible wavelength of 350 nm to 800 nm. The R light source 22r mainly emits a red laser beam R at a predetermined intensity. The G light source 22g emits a green laser beam G at a predetermined intensity. The B light source 22b emits a blue laser beam B at a predetermined intensity.

Each of the dichroic mirrors $23a_1$ and $23a_2$ transmits a laser beam having a specific wavelength band but reflects a laser beam having a wavelength band other than the specific wavelength band.

The lens system 23c focuses a laser beam comprising the laser beams R, G, and B on the measurement point in the tube 30. The laser drivers 34r, 34g, and 34b drive the R light source 22r, the G light source 22g, and the B light source 22b respectively.

The power splitter 35 distributes a supplied signal to the laser drivers 34r, 34g, and 34b.

The light sources that emit a laser beam can be composed of, for example, a semiconductor laser.

The dichroic mirror $23a_1$ is a mirror that transmits the laser beam R but reflects the laser beam G. The dichroic mirror $23a_2$ is a mirror that transmits the laser beam R and the laser beam G but reflects the laser beam B.

Such a configuration as described above makes it possible to combine the laser beams R, G, and B into an irradiation beam with which the sample 12 passing through the measurement point is irradiated.

The laser drivers 34r, 34g, and 34b are connected to the processing unit 28 and the control unit 29 and are configured to adjust the intensities of the laser beams R, G, and B emitted from the light sources 22r, 22g, and 22b.

Each of the R light source 22r, the G light source 22g, and the B light source 22b oscillates at a predetermined wavelength band so that the laser beams R, CT, and B can excite fluorochromes and the fluorochromes can emit fluorescence having specific wavelength bands. The fluorochromes excited by the laser beams R, G, and B are attached to the sample 12 to be measured such as a biological material. Therefore, when the sample 12 to be measured passes through the measurement point in the flow cell body 31, the fluorochromes are irradiated with the laser beams R, G, and B at the measurement point and emit fluorescence at specific wavelengths.

The light-receiving unit 24 is provided on the opposite side of the tube 30 and the flow cell body 31 from the laser light source unit 22. The light-receiving unit 24 is equipped with photoelectric converters that detect forward-scattered laser light from the sample 12 passing through the measurement point and outputs detection signals, one of which informs the passage of the sample 12 through the measurement point. The signals outputted from the light-receiving unit 24 are supplied to the processing unit 28 and the control unit 29 and are used in the processing unit 28 as a trigger signal informing the timing of passage of the sample 12 through the measurement point in the tube 30.

Figure 3:
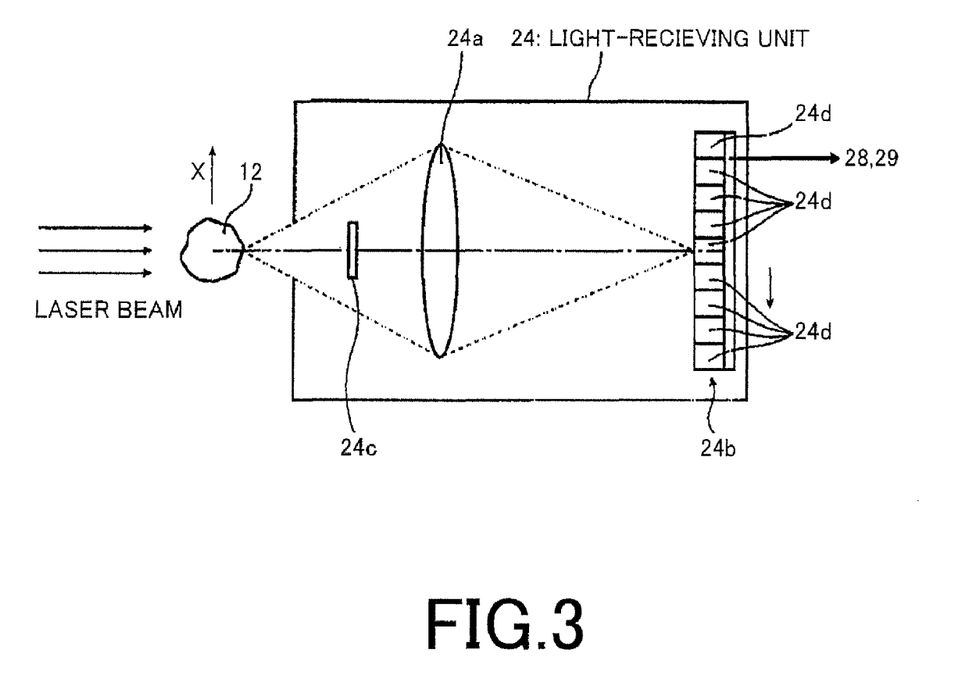
FIG. 3 is a schematic view illustrating the composition of one example of a first light-receiving unit used in the fluorescence detection device according to the present invention.

FIG. 3 is a schematic view illustrating the composition of one example of the light-receiving unit 24. In FIG. 3, a direction in which the sample 12 flows is perpendicular to the plane of paper.

The light-receiving unit 24 includes a collecting lens 24a that collects forward-scattered light produced when a laser beam strikes the sample 12, a multichannel forward-scattered light detection unit 24b that detects light focused by the collecting lens 24a, and a shielding plate 24c.

The collecting lens 24a is used to collect light scattered forward (i.e., in the traveling direction of a laser beam, more specifically, in the right-hand side direction in FIG. 3) when a laser beam strikes the sample 12.

The forward-scattered light detection unit 24b has a plurality of detectors 24d arranged side by side in a direction perpendicular to the emission direction of a laser beam and to a direction in which the sample 12 flows (i.e., in FIG. 3, a direction perpendicular to the plane of paper). Each of the detectors 24d is connected to the processing unit 28 and the control unit 29 so that detection signals can be outputted to them. All the detectors 24d have the same structure and are composed of, for example, a photodiode. The reason why the detectors 24d are arranged side by side is to obtain information about the displacement of the sample 12 when passing through a predetermined measurement point (i.e., through a focus point of a laser beam) from the center of the measurement point. More specifically, in a case where the sample 12 is displaced in an X direction illustrated in FIG. 3 when passing through the measurement point, forward-scattered light produced when a laser beam strikes the sample 12 is focused on a position lower than the central position A of the scattered-light detection unit 24b illustrated in FIG. 3 (i.e., on a position located in a direction indicated by an arrow in FIG. 3). On the other hand, in a case where the sample 12 is displaced in a direction opposite to the X direction illustrated in FIG. 3 when passing through the measurement point, forward-scattered light produced when a laser beam strikes the sample 12 is focused on a position above the central position A of the scattered-light detection unit 24b illustrated in FIG. 3. The focus position of forward-scattered light varies depending on the amount of displacement of the sample 12 in the X direction. Therefore, the focus position of forward-scattered light can be determined by determining which of the detectors 24d has detected the highest intensity of scattered light. Thereby the amount of displacement of the sample 12 to be measured from the center of the measurement point can be determined at the time when the sample 12 passes through the measurement point. The detectors 24d that have measured forward-scattered light supply detection signals to the processing unit 28 and the control unit 29. Since the detection signals are outputted from the detectors 24d, which of the detectors 24d has detected the highest intensity of forward-scattered light can be determined by identifying a detection signal having the highest level. The detection signal is used as a trigger signal for starting data processing.

The shielding plate 24c is used to block the direct light of a laser beam emitted from the laser light source unit 22 to prevent the direct light from being received by the detectors 24d.

On the other hand, the light-receiving unit 26 is arranged in a direction perpendicular to the stream of the sample 12 in a plane perpendicular to the optical axis of a laser beam emitted from the laser light source unit 22, that is, in a direction perpendicular to the emission direction of the laser beam and to the moving direction of the sample 12 in the flow channel of the flow cell body 31. The light-receiving unit 26 is equipped with a photoelectric converter that receives fluorescence emitted from the sample 12 irradiated with a laser beam at the measurement point.

On the other hand, the light-receiving unit 26 is arranged in a direction perpendicular to the emission direction of a laser beam emitted from the laser light source unit 22 and to the moving direction of the sample 12 in the flow channel of the flow cell body 31. The light-receiving unit 26 is equipped with a photoelectric converter that receives fluorescence emitted from the sample 12 irradiated with a laser beam at the measurement point.

Figure 4:
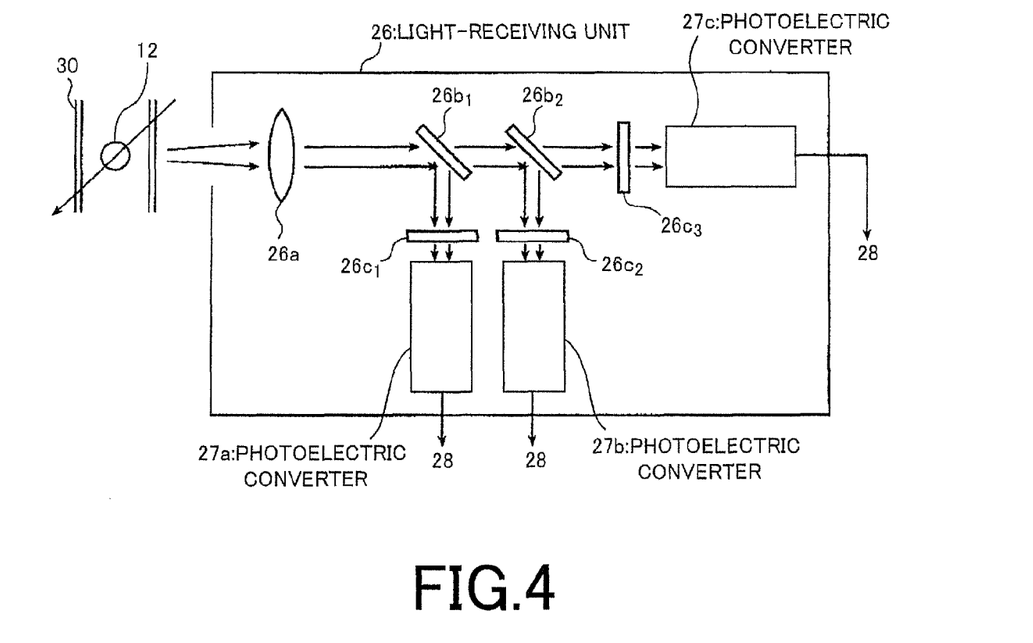
FIG. 4 is a schematic view illustrating the composition of one example of a second light-receiving unit used in the fluorescence detection device according to the present invention.
Figure 5A:
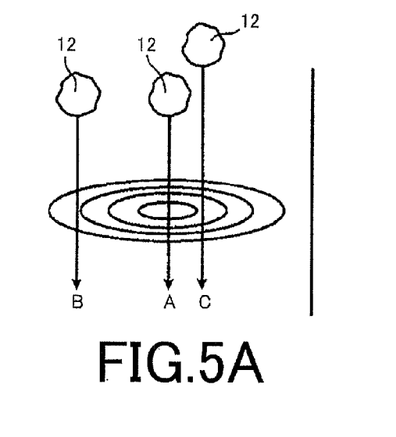
FIGS. 5A to 5E are illustrations for explaining correction performed by the fluorescence detection device according to the present invention.
Figure 5B:
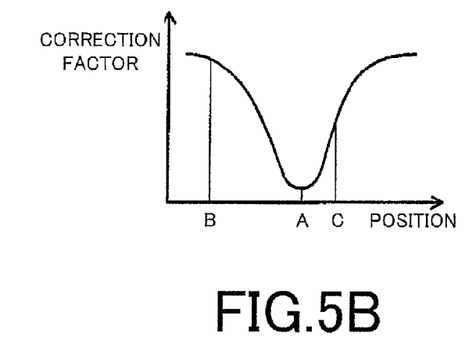
Figure 5C:
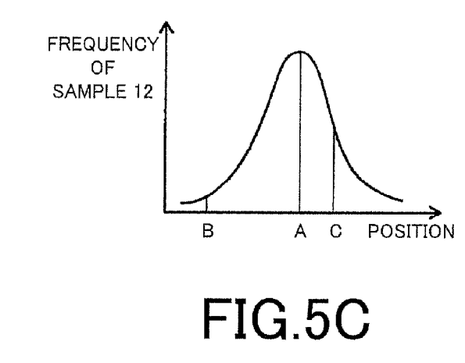
Figure 5D:
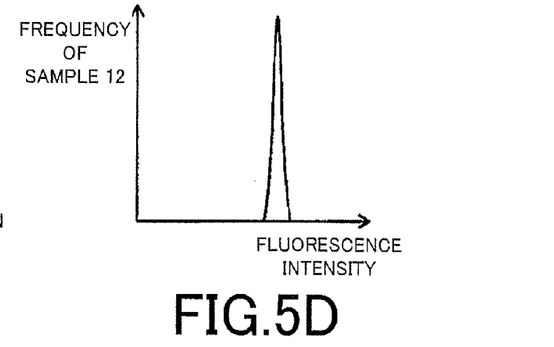
Figure 5E:
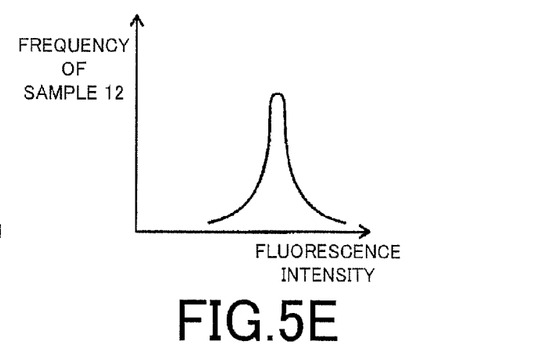

FIG. 4 is a schematic view illustrating the composition of one example of the light-receiving unit 26.

The light-receiving unit 26 illustrated in FIG. 4 includes a lens system 26a that focuses a fluorescence signal from the sample 12, dichroic mirrors $26b_1$ and $26b_2$, band pass filters $26c_1$ to $26c_3$, and photoelectric converters 27a to 27c such as photoelectric multiplier tubes.

The lens system 26a is configured to focus fluorescence incident on the light-receiving unit 26 onto light-receiving surfaces of the photoelectric converters 27a to 27c.

Each of the dichroic mirrors $26b_1$ and $26b_2$ is a mirror that reflects fluorescence having a predetermined wavelength band but transmits other fluorescence. The reflection wavelength band and transmission wavelength band of each of the dichroic mirrors $26b_1$ and $26b_2$ are set so that fluorescence having predetermined wavelength bands can be received by the photoelectric converters 27a to 27c by filtering using the band pass filters $26c_1$ to $26c_3$.

Each of the band pass filters $26c_1$ to $26c_3$ is a filter that transmits only fluorescence having a predetermined wavelength band, and is provided in front of the light-receiving surfaces of the photoelectric converters 27a to 27c. The wavelength bands of fluorescence that can pass through the band pass filters $26c_1$ to $26c_3$ are set so as to correspond to the wavelength bands of fluorescence emitted from the fluorochromes.

Each of the photoelectric converters 27a to 27c is a sensor equipped with, for example, a photoelectric multiplier tube, and converts light received by its photoelectric surface into an electric signal.

The control unit 29 is a unit that allows the laser light source unit 22 to emit a laser beam at a predetermined intensity and controls various processing operations performed by the processing unit 28 based on a trigger signal supplied from the light-receiving unit 24.

The processing unit 28 is a unit that performs predetermined signal processing to output an output value of fluorescence intensity to the analyzer 80.

The processing unit 28 starts predetermined data processing based on one of the detection signals supplied from the light-receiving unit 24. More specifically, the processing unit 28 identifies which of the detectors 24d of the light-receiving unit 24 has outputted a detection signal having the highest level, and based on the result, determines the focus position of forward-scattered light. Then, based on the thus determined focus position of forward-scattered light, the processing unit 28 determines a correction factor for correcting a light-reception signal outputted from the light-receiving unit 26, and corrects the light-reception signal using the correction factor.

The processing unit 28 collectively performs processing to determine the intensity of a laser beam based on the focus position detected using the detectors 24d and processing to determine a correction factor depending on the thus determined intensity of a laser beam, and therefore performs the correction of a light-reception signal using a previously-stored correction table. This correction table is obtained by making a linkage between the focus position of forward-scattered light and a correction factor for correcting a light-reception signal based on information about the light intensity distribution of a laser beam with which the sample 12 is irradiated.

FIGS. 5(*a*) to 5(*e*) are illustrations for explaining the necessity for performing correction on a light-reception signal.

In the present invention, a light-reception signal is used to calculate such a frequency distribution of fluorescence intensity from the sample 12 as illustrated in FIG. 5(*d*) in the analyzer 80 (which will be described later). This frequency distribution is used to determine whether or not specific fluorescence has been measured. In a case where two kinds of fluorescence are emitted, two peaks appear in a frequency distribution. When having similar fluorescence intensities, these two peaks need to have a small width (i.e., a low variance) in order to discriminate them from each other. As illustrated in FIG. 5(*e*), in a case where the width of each peak is large (i.e., in a case where each peak has a high variance), adjacent two peaks cannot be discriminated from each other. The frequency distribution illustrated in FIG. 5(*e*) is not subjected to the above-described correction.

The correction of a light-reception signal is performed by multiplying the light-reception signal by a correction factor, having the inverse distribution of the light intensity distribution of a laser beam, determined depending on the position (e.g., A to C illustrated in FIG. 5(*a*)) of the sample 12 at the time when the sample 12 passes through the measurement point. As illustrated in FIG. 5(*c*), the position of the sample 12 at the time where the sample 12 passes through the measurement point is variable. However, as compared to the frequency distribution illustrated in FIG. 5(*e*) not subjected to correction, the width of a peak can be made smaller as illustrated in FIG. 5(*d*) by correcting a light-reception signal in such a manner as described above using a correction factor.

As described above, the correction of a light-reception signal is performed to reduce a peak width as illustrated in FIG. 5(*d*) to improve the resolution of a frequency distribution.

Such correction is performed by simply multiplying a light-reception signal by a correction factor. This is because part of a fluorescence signal whose intensity is linearly changed depending on the intensity of a laser beam, with which the sample 12 is irradiated, is properly used as a light-reception signal. However, the present invention is not limited thereto as long as at least fluorescence intensity has a correlation with the light intensity of a laser beam, with which the sample 12 is irradiated, and a correction factor is determined based on the correlation between the fluorescence intensity and the light intensity of the laser beam.

The analyzer 80 is a device that creates such a frequency distribution as illustrated in FIG. 5(*d*) using a corrected light-reception signal supplied from the processing unit 28 and identifies, for example, the type of a biological material contained in the sample 12 passing through the measurement point in the flow cell body 31 to analyze the biological material contained in the sample 12.

In such a fluorescence detection device 10 as described above, forward-scattered light emitted from the sample 12 by irradiation with a laser beam is detected by the detectors 24d of the scattered-light detection unit 24b. The focus position of the forward-scattered light can be determined from detection signals outputted by the detectors 24d. Based on the thus determined focus position, a correction factor can be determined using a correction table stored in the processing unit 28. A light-reception signal outputted by the light-receiving unit 26 is corrected by multiplying the light-reception signal by the correction factor.

The corrected light-reception signal is supplied to the analyzer 80 to create such a frequency distribution as illustrated in FIG. 5(*d*).

The processing unit 28 of the fluorescence detection device 10 performs correction of a light-reception signal using a correction table using the distribution of laser light intensity, and therefore the analyzer 80 can create a frequency distribution having a small peak width. Further, unlike a conventional fluorescence detection device using only the central portion of a laser beam where the intensity is uniform to measure fluorescence, the fluorescence detection device 10 can use not only the central portion of a laser beam but also the outer portion of the laser beam, which is not conventionally used for fluorescence measurement, to measure fluorescence because even when the laser beam has an intensity distribution, a light-reception signal is corrected using the intensity distribution. This makes it possible to efficiently use a laser beam.

Further, the position of the sample 12 at the time when the sample 12 passes through the measurement point can also be determined. The light intensity of a laser beam at the position of the sample 12 has been already determined from detection signals outputted by the detectors 24d. On the other hand, the size of the measured sample 12 can also be determined using the already-determined light intensity of a laser beam, because the light intensity of forward-scattered light is determined as a result of multiplying, by the size of the sample 12, the light intensity of a laser beam at the position of the sample 12 at the time when the sample 12 passes through the measurement point. The analyzer 80 may perform such processing to calculate the size of the measured sample 12. In this case, the size of the sample 12 is determined using the intensity of a scattered-light signal of forward-scattered light outputted from the light-receiving unit 24 and the focus position of the forward-scattered light. More specifically, since the focus position of forward-scattered light has already been determined, the amount of displacement of the sample 12 from the center of the measurement point at the time when the sample 12 passes through the measurement point is determined from the already-determined focus position to determine the light intensity of a laser light with which the sample 12 displaced from the center of the measurement point has been irradiated. The size of the sample 12 can be determined from the thus determined light intensity of a laser beam and the intensity of a scattered-light signal of forward-scattered light.

Although the fluorescence detection device and the fluorescence detection method according to the present invention have been described above in detail, the present invention is not limited to the above embodiment and various changes and modifications may be made without departing from the scope of the present invention.

What is claimed is:

1. A fluorescence detection device for measuring fluorescence emitted from a measurement object flowing through a flow channel by irradiation with a laser light, comprising:
    a laser light source unit that irradiates, with a laser beam, a measurement object passing through a measurement point in a flow channel;
    a first light-receiving unit comprising an optical system that collects forward-scattered laser light from the measurement object and a plurality of detectors arranged side by side in a direction perpendicular to a direction of an optical axis of the laser beam and to a direction in which the measurement object flows through the flow channel in order to receive the collected forward-scattered light to inform the timing of passage of the measurement object through the measurement point and to detect a focus position of the collected forward-scattered light;
    a second light-receiving unit that receives, through a collecting lens, fluorescence emitted from the measurement object irradiated with the laser beam and outputs a light-reception signal; and
    a processing unit that uses one of detection signals outputted from the first light-receiving unit as a trigger signal to start data processing performed based on the light-reception signal outputted from the second light-receiving unit and the detection signals, and outputs an output value of fluorescence intensity,
    wherein the processing unit identifies a focus position of the forward-scattered light by finding a signal of a highest output level among the detection signals outputted from the first light-receiving unit and determines, based on the thus determined focus position, a correction factor for correcting the light-reception signal outputted from the second light-receiving unit, and corrects the light-reception signal using the correction factor.

2. The fluorescence detection device according to claim 1, wherein the processing unit determines the correction factor using a correction table obtained by making a linkage between the focus position and the correction factor for correcting a light-reception signal based on information of light intensity distribution of the laser beam with which the measurement object is irradiated.

3. The fluorescence detection device according to claim 1, further comprising a shielding plate provided between the flow channel and the first light-receiving unit to block a portion of the laser beam around an optical axis of the laser beam to prevent the first light-receiving unit from being irradiated with direct light of the laser beam.

4. The fluorescence detection device according to claim 1, further comprising an analyzer that creates a frequency distribution of fluorescence intensity using the corrected light-reception signal when a plurality of measurement objects are allowed to flow through the flow channel one after another.

5. The fluorescence detection device according to claim 1 further comprising an analyzer that determines a size of the measurement object using an intensity of a scattered-light signal of the forward-scattered light outputted from the first light-receiving unit and the focus position of the forward-scattered light.

6. A fluorescence detection method of measuring fluorescence emitted from a measurement object flowing through a flow channel by irradiation with a laser light, comprising the steps of:
    irradiating, with a laser light, a measurement object allowed to flow through a flow channel so as to pass through a measurement point in the flow channel;
    producing detection signals for detecting a focus position of forward-scattered laser light collected by an optical system, by using a plurality of detectors arranged side by side in a direction perpendicular to a direction of an optical axis of the laser light and to a direction in which the measurement object flows through the flow channel, when the measurement object passes through the measurement point;
    receiving, through a collecting lens, fluorescence emitted from the measurement object irradiated with the laser beam and outputting a light-reception signal; and
    identifying a focus position of the forward-scattered light by finding a signal of a highest output level among the detection signals, and determining, based on the thus identified focus position, a correction factor for correcting the light-reception signal, and correcting the light-reception signal using the correction factor to calculate fluorescence intensity.

7. The fluorescence detection method according to claim 6, wherein when the light-reception signal is corrected, the correction factor is determined using a correction table obtained by making a linkage between the focus position and the correction factor for correcting a light-reception signal based on information about light intensity distribution of the laser beam with which the measurement object is irradiated.

8. The fluorescence detection method according to claim 6, further comprising the step of creating a frequency distribution of fluorescence intensity using the corrected light reception signal when a plurality of measurement objects are allowed to flow through the flow channel one after another.

9. The fluorescence detection method according to claim 6 further comprising the step of determining a size of the measurement object using an intensity of a scattered-light signal of the forward-scattered light and the focus position of the forward-scattered light.

* * * * *